United States Patent
Sun et al.

(10) Patent No.: US 10,137,160 B2
(45) Date of Patent: Nov. 27, 2018

(54) **USE OF *HUMULUS JAPONICUS* EXTRACT FOR TREATING OBESITY OR HYPERLIPIDEMIA**

(71) Applicants: Yuan Lu Sun, Seoul (KR); Ji Hoon Jeong, Uiwang-si (KR)

(72) Inventors: Yuan Lu Sun, Seoul (KR); Ji Hoon Jeong, Uiwang-si (KR)

( * ) Notice: Subject to any disclaimer, the term of this patent is extended or adjusted under 35 U.S.C. 154(b) by 334 days.

(21) Appl. No.: 14/480,027

(22) Filed: Sep. 8, 2014

(65) Prior Publication Data

US 2014/0377383 A1  Dec. 25, 2014

Related U.S. Application Data

(63) Continuation of application No. PCT/KR2013/001862, filed on Mar. 7, 2013.

(30) Foreign Application Priority Data

Mar. 7, 2012 (KR) .......................... 10-2012-0023431

(51) Int. Cl.
*A61K 36/185* (2006.01)
*A23L 33/00* (2016.01)

(52) U.S. Cl.
CPC ............ *A61K 36/185* (2013.01); *A23L 33/40* (2016.08)

(58) Field of Classification Search
None
See application file for complete search history.

(56) References Cited

U.S. PATENT DOCUMENTS

| | | |
|---|---|---|
| 2006/0018867 A1 | 1/2006 | Kawasaki et al. |
| 2006/0165636 A1 | 7/2006 | Hasebe et al. |
| 2008/0160109 A1 | 7/2008 | Dryer et al. |
| 2010/0055060 A1 | 3/2010 | Yoshida et al. |

FOREIGN PATENT DOCUMENTS

| | | | |
|---|---|---|---|
| KR | 10-2011-0055940 | | 5/2011 |
| KR | 10-1043509 | | 6/2011 |
| KR | 20110093513 A | * | 8/2011 |
| KR | 10-2011-0093513 | | 9/2011 |

OTHER PUBLICATIONS

Carr (2003) J. Clin. Endocrinol. Metab. 88: 2404-2411.*
Website document entitled: "Causes of Diabetes" (available at http://www.niddk.nih.gov/health-information/health-topics/Diabetes/causes-diabetes). Downloaded from website Feb. 2, 2016.*
Website document entitled "Metabolic Disorders" (available at https://www.nlm.nih.gov/medlineplus/metabolicdisorders.html). Downloaded Feb. 2, 2016.*
Yajima et al. (2005) International Journal of Obesity 29, 991-997.*
Fernandez-Alonso, et al. (2010) Menopause International, 16; 105-110.*
Begum et al. (2009) International Seminars in Surgical Oncology, 6:1-5.*
Cleemput et al. (2009) J. Nat. Prod. 72, 1220-1230.*
Gravena et al. (2013) BMC Women's Health, 13: 46.*
Lobo (2008) Maturitas 60: 10-18.*
Obara et al. (2009) Clinical Nutrition 28; 278-284.*
Raskin et al. (2004) Current Pharmaceutical Design, 10: 3419-3429.*
Revilla et al. (1998) J. Agric. Food Chem. 46, 4592-4597.*
Shimura et al. (2005) Biochimica et Biophysica Acta 1736: 51-60.*
Yajima et al. (2004) JBC vol. 279, No. 32, pp. 33456-33462.*
International Search Report dated Jun. 14, 2013 in International Application No. PCT/KR2013/001862.
Written Opinion dated Jun. 14, 2013 in International Application No. PCT/KR2013/001862.
Matsuzawa et al., "Pathophysiology and Pathogenesis of Visceral Fat Obesity", Obesity Research, vol. 3, Supp. 2 (Sep. 1995), pp. 187s-194s.
Assy et al., "Fatty infiltration of liver in hyperlipidemic patients", Digestive Diseases and Sciences, vol. 45(10), Oct. 2000, pp. 1929-1934.

* cited by examiner

*Primary Examiner* — Christopher R Tate
*Assistant Examiner* — Russell G Fiebig
(74) *Attorney, Agent, or Firm* — H.C. Park & Associates, PLC

(57) ABSTRACT

A functional health food containing *Humulus japonicus* extract as an active ingredient for preventing or improving metabolic disorders or for weight loss, a pharmaceutical composition containing *Humulus japonicus* extract as an active ingredient for preventing or treating metabolic disorders, a functional health food containing *Humulus japonicus* extract as an active ingredient for preventing or improving fatty liver, and a functional health food containing *Humulus japonicus* extract as an active ingredient for inhibiting the accumulation of visceral fat.

3 Claims, 10 Drawing Sheets

USE OF *HUMULUS JAPONICUS* EXTRACT FOR TREATING OBESITY OR HYPERLIPIDEMIA

CROSS REFERENCE TO RELATED APPLICATIONS

This application is a continuation of International Application No. PCT/KR2013/001862, filed Mar. 7, 2013, and claims priority from Korean Patent Application No. 10-2012-0023431, filed Mar. 7, 2012, all of which are hereby incorporated by reference for all purposes as if fully set forth herein.

BACKGROUND

Field

The present invention relates to the use of a *Humulus japonicus* extract for preventing or treating metabolic disorders or fatty liver, and more particularly, to a functional health food containing a *Humulus japonicus* extract as an active ingredient for preventing or improving metabolic disorders or for losing weight; to a pharmaceutical composition containing a *Humulus japonicus* extract as an active ingredient for preventing or treating metabolic disorders; to a functional health food or a pharmaceutical composition containing a *Humulus japonicus* extract as an active ingredient for preventing or improving fatty liver; and to a functional health food containing a *Humulus japonicus* extract as an active ingredient for inhibiting the accumulation of visceral fat.

Discussion of the Background

*Humulus japonicus* S. et Z., which is also called Japanese hop or *Humulus scandnes Merr.*, has the efficacy of lowering the fever, facilitating urination, removing extravasated blood, and detoxificating the body. It has been reported to treat gonorrhea, dysuria, malaria, diarrhea, dysentery, tuberculosis, lung abscess, pneumonia, Hansen's disease, haemorrhoids, abscess, and scrofula. Bencao Gangmu (Compendium of Materia Medica) describes that it smoothens triple energizers, helps the digestion of five grains, supports five viscera, kills various worms in the abdomen, and treats murrain.

*Humulus japonicus* is a perennial plant from the hemp family, and leaves thereof look like leaves of the hemp or leaves of the hop which is used as a raw material for manufacturing beer. The leaves grow sub-oppositely, have long and ovate petioles, with being palmate with 5-7 lobes. The leaf margins have a long oval shape and are bluntly toothed. Male and female flowers are borne on separate plants. The plants are in bloom and out of bloom, repeatedly, from May to September, and then produce small, rounded fruits in autumn. Stems wither in the autumn, but the roots are alive even in the winter. These tenaciously strong stems are very sturdy and have numerous fine thorns adhering thereto. Thus, if scratched by the stems, a person's hands or face become very itchy and damaged. These sturdy stems are often used to make natural fibers. *Humulus japonicus* is assumed not to be native to Korea but imported from other foreign countries, and grows well in barren soil.

Recently, the improved standards of living due to economic development have improved environmental hygiene, while frequent consumption of instant food and meat-oriented dietary change have lead to the accumulation of excessive calories in one's body. However, this dietary change of modern people has been causing a fast rise in obesity together with the reduction in calorie consumption due to lack of exercise.

As such, the calories excessively accumulated in the body cause obesity and various diseases including metabolic disorders, such as diabetes, hyperlipidemia, and hypertension.

Obesity is the single most dangerous disease and causes the highest fatality in the 21$^{st}$ century. The reason is that obesity is dangerous per se, and also often causes constipation, indigestion, gastroenteric troubles and the like due to the abdominal pressure by fat tissues, while significantly increasing the risks of various other diseases. Representative diseases that are at their higher risk of developing due to obesity are type 2 diabetes, hypertension, coronary artery diseases, stroke, and various cancers.

Thus, there is a growing need for solving obesity-related problems through medicine intakes or dietary control. Anti-obesity drugs may be used for the treatment of obesity. However, contemporary anti-obesity drugs are problematic because of their side effects. It is a common knowledge that many products which have been currently used as a medicinal treatment of obesity show side effects and cause many social problems.

Diabetes is a kind of systemic metabolic disorder resulting from genetic and environmental factors, and refers to a state in which an abnormally high glucose concentration in blood is caused by absolute and relative insulin deficiency in the body. The complications of diabetes include hypoglycemia, ketoacidosis, hyperosmolar coma, macrovascular complications, diabetic retinopathy, diabetic neuropathy, diabetic nephropathy, and the like.

Hyperlipidemia includes both hypercholesterolemia and hypertriglycerides, and refers to a state in which cholesterol (240 mg/dl or more) and triglycerides (200 mg/dl or more) increase above their normal ranges due to disorders of lipoprotein and lipid metabolism. Hyperlipidemia is largely classified into primary hyperlipidemia resulting from genetic abnormalities and secondary hyperlipidemia resulting from other diseases, such as diabetes, or drugs. Hyperlipidemia does not develop any particular symptom, but has a problem in that increase in the levels of cholesterol and triglycerides in the blood may cause arteriosclerosis, hypertension, cardiovascular diseases, and the like.

The main medications used to treat hyperlipidemia include statins, bile acid blockers, fibric acid derivatives, and the like, which need to be orally administered daily for a long period of time. These medications effectively lower the levels of cholesterol and blood lipid, but have their side effects. Startins may cause nausea, headache, abdominal pain, diarrhea, or constipation, and may cause myositis. The bile acid blockers may lower the absorption of vitamins A, D, and K into the intestine, thus requiring the supplementation of the above vitamins. The fibric acid derivatives are unsuitable for those having kidney disease, liver disease, or gallbladder disease. Therefore, the demands for the development of functional foods containing medicinal and natural materials substituting for those above agents are increasing (Kook Seungrae et. al, Korean Journal of Family Medicine, 18(3), pp. 317-327, 1997).

Meanwhile, it has been recently reported that non-alcoholic fatty liver disease is associated with cardiovascular diseases (CVD) including artherosclerosis, cerebrovascular diseases (Francazani A et al., Am J Med 2008, 121:72-78), microvascular diseases, nephropathy, and retinopathy (Targher G et al., Diabetologia 2008; 51(3):444-450), polycystic ovarian syndrome (PCOS) (Targher Get al., Atherosclerosis 2007, 191:235-240, Cerda C et al., J Hepatol 2007, 47:412-417), or obstructive sleep apnea (OSA) (Tanne F at al., Hepatology 2005, 41:1290-1296).

Currently, there is no established treatment for non-alcoholic fatty liver disease since it is associated with various factors, such as diabetes, obesity, coronary artery diseases, and sedentary habits. Obesity is the important target for treating the non-alcoholic fatty liver disease since alleviating obesity may induce the reduction in factors related to insulin resistance, which is a liver damage risk factor, the amount of fatty acid entering into the liver, and inflammatory or fibrous adipokine. Weight loss by dietary control and exercise may reduce the levels of alanine aminotransferase (ALT) and triglyceride in the liver. There have been few reports showing that weight loss may lead to any improvement in patients with hepatic fibrosis or necrotic inflammation (Harrison S A et al., Gut 2007, 56:1760-1769).

SUMMARY

While researching natural extracts with no side effects in order to treat metabolic disorders, fatty liver, and the like, the present inventors have found that a *Humulus japonicus* extract has such an efficacy, and then completed the present invention.

Therefore, an aspect of the present invention is to provide a functional health food or a pharmaceutical composition containing a *Humulus japonicus* extract as an active ingredient for preventing, improving or treating metabolic disorders.

Another aspect of the present invention is to provide a use of a *Humulus japonicus* extract for preparing an agent for preventing or treating metabolic disorders.

Another aspect of the present invention is to provide a method for preventing or treating metabolic disorders, comprising administering an effective amount of a *Humulus japonicus* extract to a subject in need thereof.

Another aspect of the present invention is to provide a functional health food containing a *Humulus japonicus* extract as an active ingredient for weight loss.

Another aspect of the present invention is to provide a functional health food or a pharmaceutical composition containing a *Humulus japonicus* extract as an active ingredient for preventing, improving or treating fatty liver.

Another aspect of the present invention is to provide a use of a *Humulus japonicus* extract for preparing an agent for preventing or treating fatty liver.

Another aspect of the present invention is to provide a method for preventing or treating fatty liver, comprising administering an effective amount of *Humulus japonicus* extract to a subject in need thereof.

Another aspect of the present invention is to a functional health food containing a *Humulus japonicus* extract as an active ingredient for inhibiting the accumulation of visceral fat.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawings will be provided by the office upon request and payment of the necessary fee.

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

*Humulus japonicus* is a vine perennial plant from the hemp family and is a weed that commonly grows in wild fields. The main stem and petiole have downward fine thorns and thus are rough. Flowers bloom in July to August and are dioecious. A staminate flower has 5 calyxes and 5 stamens, sticking to a panicle. A pistillate flower is attached to a spike. A bract grows after the blooming of the flower and has an oval circular shape with a length of 7-10 mm. Fruits are produced through September to October. An achenium has an oval circular shape, yellow brown color, and fine hairs on the upper part. The ocrea of the stem is used as fibers, fruit is used as bitter stomachic, and the whole plant with fruit is used as diuretic. It is widely distributed in Korea, Japan, Taiwan, and China.

Figure 1:
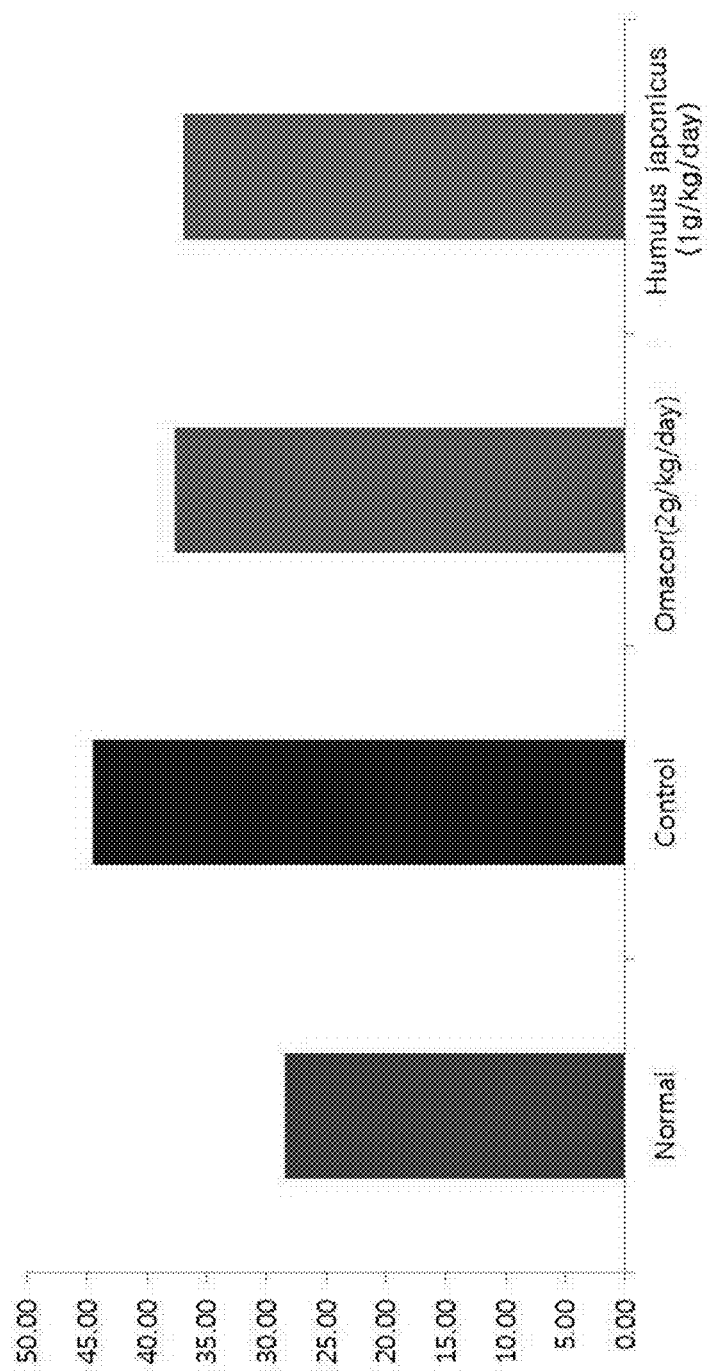
FIG. 1 is a graph depicting the comparison of body weight change among respective experimental groups. (Y-axis unit: g (gram)/X axis: Normal (normal group), Control (obesity control group, Omacor (Omacor-administered group), *Humulus japonicus* (*Humulus japonicas*-administered group))
Figure 2:
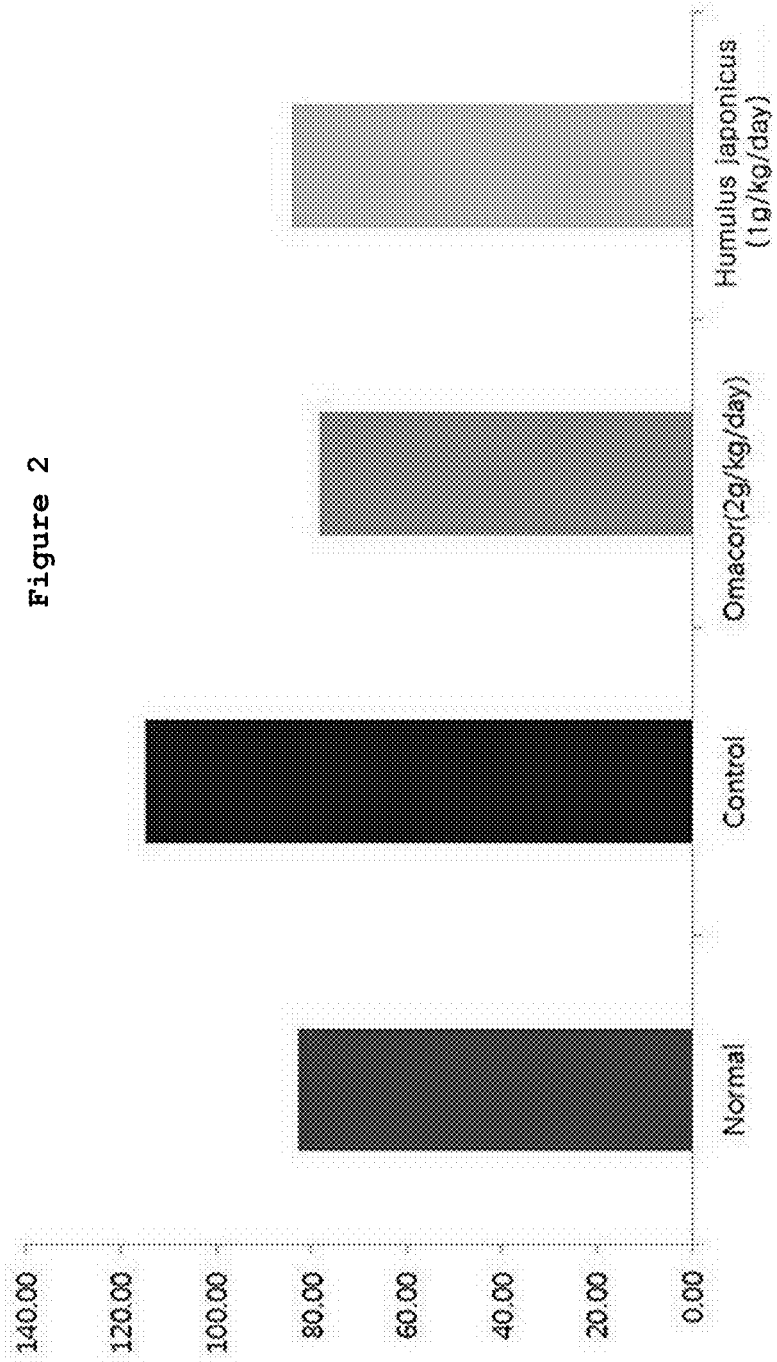
FIG. 2 is a graph depicting the comparison of blood TG level among respective experimental groups. (Y-axis unit: mg/dl/X axis: Normal (normal group), Control (obesity control group, Omacor (Omacor-administered group), *Humulus japonicus* (*Humulus japonicas*-administered group))
Figure 3:
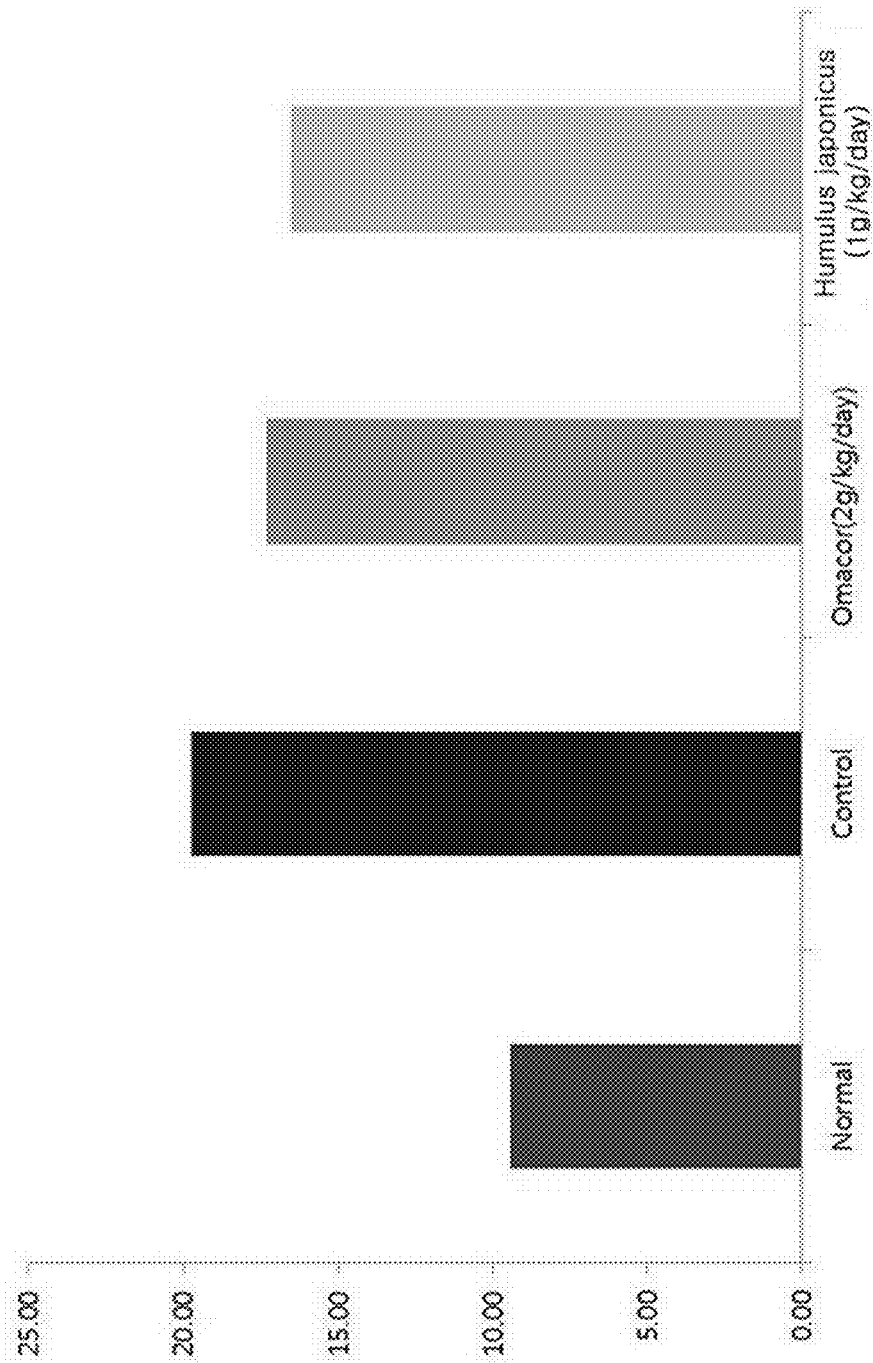
FIG. 3 is a graph depicting the comparison of blood LDL level among respective experimental groups. (Y-axis unit: mg/dl/X axis: Normal (normal group), Control (obesity control group, Omacor (Omacor-administered group), *Humulus japonicus* (*Humulus japonicas*-administered group))
Figure 4:
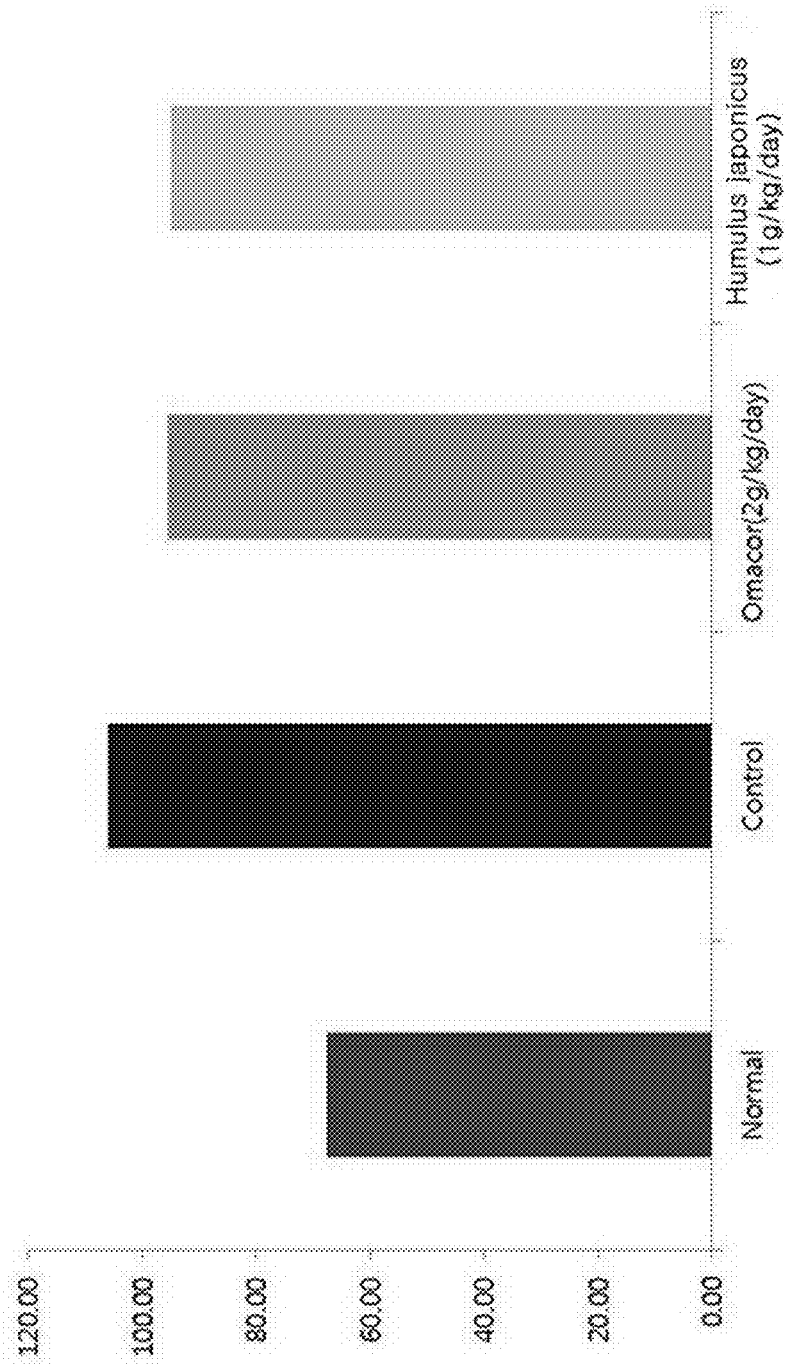
FIG. 4 is a graph depicting the comparison of blood HDL level among respective experimental groups. (Y-axis unit: mg/dl/X axis: Normal (normal group), Control (obesity control group, Omacor (Omacor-administered group), *Humulus japonicus* (*Humulus japonicas*-administered group))
Figure 5:
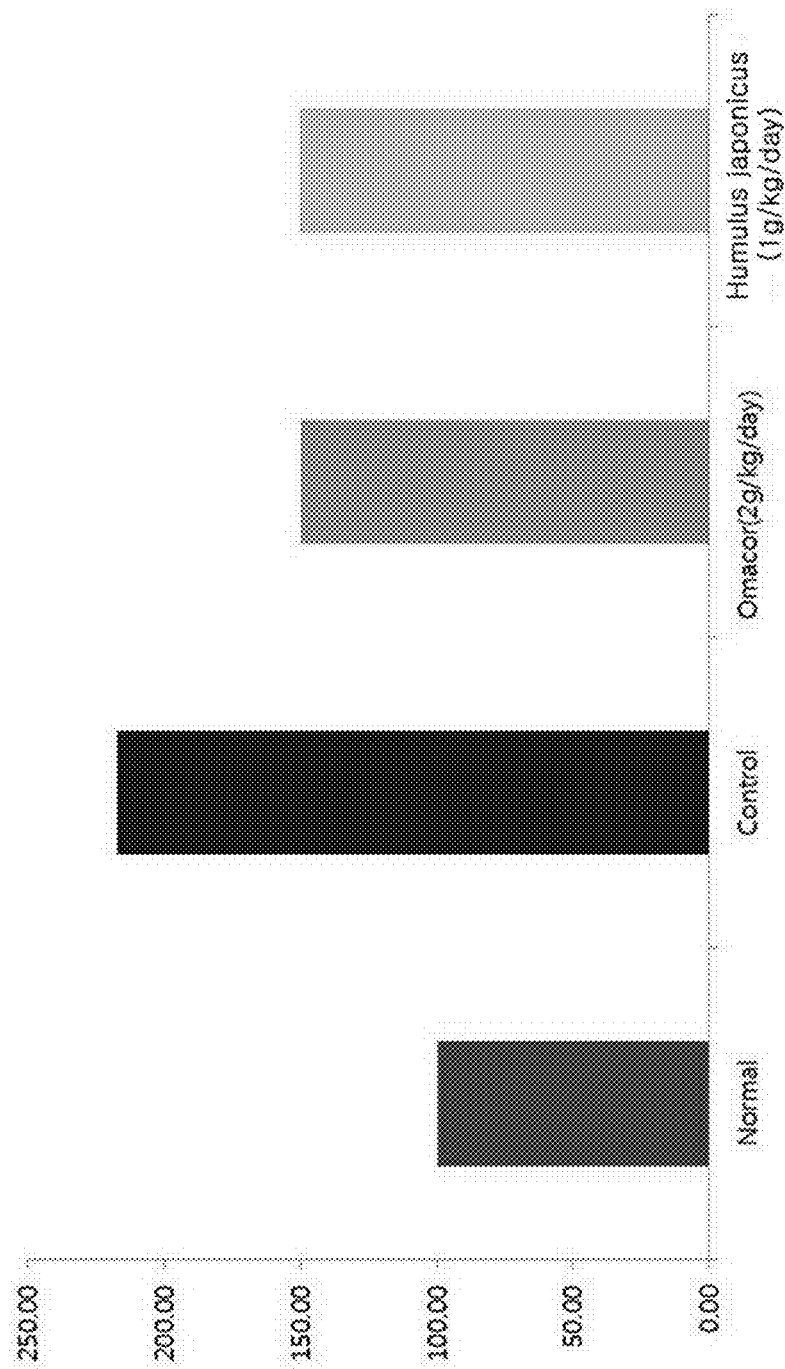
FIG. 5 is a graph depicting the comparison of blood TC level among respective experimental groups. (Y-axis unit: mg/dl/X axis: Normal (normal group), Control (obesity control group, Omacor (Omacor-administered group), *Humulus japonicus* (*Humulus japonicas*-administered group))

*Humulus japonicus* has the efficacy of treating metabolic disorders, such as hypertension, obesity, hyperlipidemia, and the like. This can be confirmed by Example 2 of the present application. FIG. 1 shows that the Omacor-administered group and the *Humulus japonicas*-administered group exhibited body weights approximating the median body weight between the normal group and the obesity control group. Even though the Omacor-administered group was administered with a higher daily dosage (2 g/kg/day), the *Humulus japonicas*-administered group (dosage: 1 g/kg/day) showed less body weight. FIG. 2 shows that the *Humulus japonicus* administered group and the normal group had similar levels of blood triglyceride, while FIG. 3 shows that the LDL level of *Humulus japonicas*-administered group and the normal group was lower than those of the obesity control group and the Omacor-administered group. FIG. 5 shows that the total cholesterol level of the *Humulus japonicas*-administered group was conspicuously lower than that of the obesity control group, while being similar to that of the Omacor-administered group. As a whole, FIGS. 2 to 5 show that the levels of the *Humulus japonicas*-administered group were similar to those of the Omacor-administered group. However, considering that the dosage of the Omacor-administered group was 2 times higher than that of the *Humulus japonicas*-administered group, the *Humulus japonicus* extract possesses more excellent efficacy than Omacor. In addition, as a result of histological observation of subcutaneous fat tissue taken from the inguinal region of mice, the size of lipocytes in the Omacor-administered group was found similar to that of the obesity control group, and the number of cells with loss of nuclei was found similar to that of the obesity control group. However, in the *Humulus japonicas*-administered group, there was a significant reduction in terms of the size of lipocytes and the number of lipocytes with loss of nuclei when compared with the obesity control group. Therefore, it was concluded that the *Humulus japonicus* extract possesses excellent effect in inhibiting the deformation and expansion of lipocytes as compared with Omacor.

Accordingly, the present invention provides a functional health food containing the *Humulus japonicus* extract as an active ingredient for preventing or improving metabolic disorders or for weight loss.

Further, the present invention provides a pharmaceutical composition containing the *Humulus japonicus* extract as an active ingredient for preventing or improving metabolic disorders.

The metabolic disorder is characterized by being selected from the group consisting of obesity, diabetes, hypertension, and hyperlipidemia.

Figure 6:
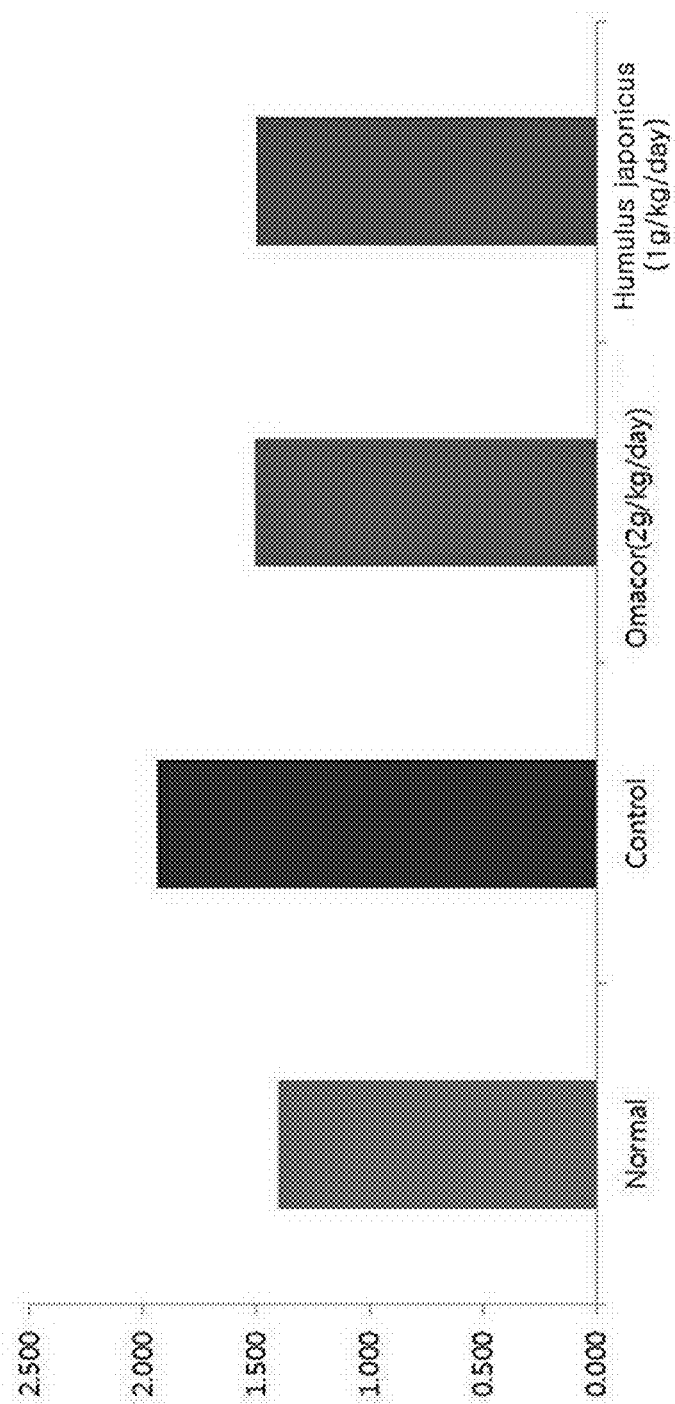
FIG. 6 is a graph depicting the comparison of liver weight among respective experimental groups. (Y-axis unit: g (gram)/X axis: Normal (normal group), Control (obesity control group, Omacor (Omacor-administered group), *Humulus japonicus* (*Humulus japonicas*-administered group))

Further, the *Humulus japonicus* extract of the present invention has an effect of preventing or improving fatty liver. This effect can be confirmed by Example 3 of the present application. Excessive consumption of fat results in the abnormal accumulation of fat in the liver, leading to fatty liver. Referring to FIG. 6, the liver weight of the obesity control group with a high-fat diet was larger than that of the normal group with a general diet. However, the liver weight of the *Humulus japonicus* administered group was similar to that of the normal group despite a high-fat diet. Alanine aminotransferase (ALT) and aspartate aminotransferase (AST) are enzymes existing in the hepatocytes, and used as liver function test indexes. These enzymes are released into the blood to increase their blood levels when the hepatocytes are damaged. Their levels may become higher when there is fatty liver or hepatitis. Referring to FIG. 7, the ALT level in the *Humulus japonicas*-administered group was significantly lower than that of the obesity control group, while being also lower than that of the Omacor-administered group. Also, when the AST levels of the *Humulus japonicas*-administered group and the obesity control group were compared, the improvement effect of the *Humulus japonicus* extract was confirmed. The direct observation of the hepatocytes confirmed an excellent efficacy of the *Humulus japonicus* extract. As a result of observing the red-stained lipid part, a large amount of red-stained lipid was found to be accumulated among the hepatocytes in the obesity control group, whereas the accumulated amount of lipid was less in the Omacor-administered group and the *Humulus japonicas*-administered group. However, it can be confirmed that the amount of the lipid was conspicuously reduced in the *Humulus japonicas*-administered group than the Omacor-administered group (see FIGS. 10A-10D).

Therefore, the present invention provides a functional health food containing the *Humulus japonicus* extract as an active ingredient for preventing or improving fatty liver.

Further, the present invention provides a pharmaceutical composition containing the *Humulus japonicus* extract as an active ingredient for preventing or improving fatty liver.

Figure 8:
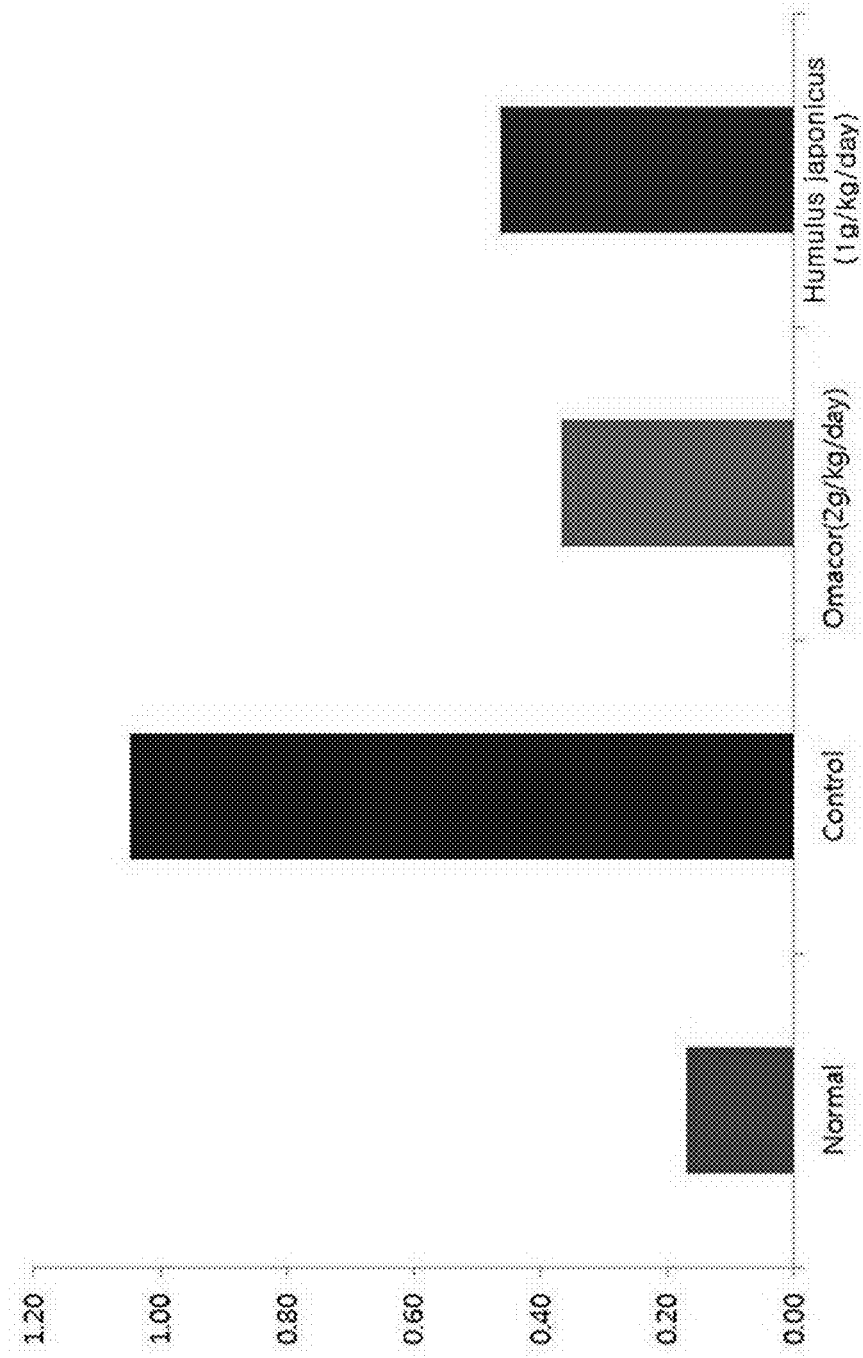
FIG. 8 is a graph depicting the comparison of mesenteric fat weight among respective experimental groups. (Y-axis unit: g (gram)/X axis: Normal (normal group), Control (obesity control group, Omacor (Omacor-administered group), *Humulus japonicus* (*Humulus japonicas*-administered group))

The *Humulus japonicus* extract of the present invention also have an efficacy of inhibiting the accumulation of visceral fat. This can be confirmed by Example 4 of the present application. The high level of visceral fat tends to increase the incidence of diabetes, heart disease, hypertension, and the like, and thus, the lower level of visceral fat is considered favorable. For the weight measurement of visceral fat, the weight of the mesenteric fat was measured. FIG. 8 confirmed that the *Humulus japonicas*-administered group had an effect of inhibiting the accumulation of visceral fat. The amount of visceral fat was excessively increased in the obesity control group than the normal group, but was significantly reduced in the *Humulus japonicas*-administered group.

Accordingly, the present invention provides a functional health food for inhibiting the accumulation of visceral fat.

The solvent used to prepare the *Humulus japonicus* extract may be preferably water, C1-C6 alcohol, or a mixture solvent thereof, and preferably water. The amount of the solvent may vary depending on the amount of *Humulus japonicus* extracted, and may be preferably 0.5 to 5 times volume (w/v %), more preferably 1-5 times volume (w/v %), and most preferably 1 time volume (w/v %) of the *Humulus japonicus*.

In addition, the extract may be liquefied through filtration, and preferably may be solidified through a drying process, such as spray-drying or freeze-drying, and more preferably freeze-drying.

The functional health food of the present invention includes all types of foods, such as various functional foods, nutritional supplements, and food additives, which have an effect of preventing or improving metabolic disorders, weight loss, or improving fatty liver. The above types of food composition may be prepared in various forms according to the common methods known in the art. For example, the food may be one in which the *Humulus japonicus* itself may be prepared in a form of tea, juice, or drink for the purpose of drinking, or may be granulated, capsulated, or powdered for the purpose of intake. Also, the food may be formulated in a composition form in which the *Humulus japonicus* extract is mixed with known active ingredients known to have an effect of improving metabolic disorders, weight loss, or improving fatty liver. Also, the food may be one prepared by adding the *Humulus japonicus* extract to beverages (including alcoholic beverages), fruits and processed foods thereof (e.g., canned fruit, bottled fruits, jam, marmalade, etc.), fish, meats and processed products thereof (e.g., ham, sausage, corned beef, etc.), breads, noodles (e.g., udong, buckwheat noodles, ramen, spaghetti, macaroni, etc.), fruit juices, a variety of drinks, cookies, syrups, dairy products (e.g., butter, cheese, etc.), edible vegetable oils, margarine, vegetable proteins, retort foods, frozen foods, and various seasonings (e.g., soybean paste, soybean sauce, sauces, etc.).

The food additive may contain the *Humulus japonicus* extract in a form of powder or concentrate. The content of *Humulus japonicus* extract in the food of the present invention may be appropriately adjusted according to the form, usage, and purpose of use of the final food, and may be for example 0.001-20 g per 100 g of food, but is not limited thereto. The food containing the *Humulus japonicus* extract of the present invention may be one prepared by mixing the *Humulus japonicus* extract with other known active ingredients known to have an effect of improving metabolic disorder, weight loss, or improving fatty liver.

The pharmaceutical composition of the present invention may contain the *Humulus japonicus* extract alone, or may further contain appropriate carriers, excipients, and diluents, which are commonly used to prepare a pharmaceutical composition.

The composition according to the present invention may be formulated in an oral dosage form, such as powder, granule, tablet, capsule, suspension, emulsion, syrup, or aerosol; an external preparation; suppository, and sterile injectable solution, according to the general method for respective formulation. Examples of carriers, excipients, and diluents that may be contained in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

Specifically, the composition may be formulated by using diluents or excipients, such as fillers, extenders, binders, wetting agents, disintegrants, or surfactants. Solid preparations for oral administration include tablet, pill, powder, granule, capsule, and the like. These solid preparations may be prepared by mixing with at least one excipient, for example, starch, calcium carbonate, sucrose or lactose, gelatin, or the like. Further, in addition to the simple excipient, lubricants such as magnesium stearate and talc may be used. Liquid preparations for oral administration include suspension, oral solution, emulsion, syrup, and the like. In addition to simple diluents such as water, liquid, and paraffin, various excipients, for example, wetting agents, sweeteners, flavoring agents, and preservatives may be contained therein. Preparations for parenteral administration include sterilized aqueous solution, non-aqueous solvent, suspension, emulsion, freeze-drying agent, and suppository. The non-aqueous solvent and suspension may include propylene glycol, polyethylene glycol, vegetable oil such as olive oil, injectable ester such as ethylolate, and the like. As a substrate for the suppository, Witepsol, Macrogol, twin 61, cacao butter, laurin butter, or glycerogelatin may be used.

A suitable dosage of the extract of the present invention may vary depending on morbidity and body weight of a patient, severity of disease, form of drug, and manner and period of administration, but may be appropriately selected by those skilled in the art. However, for producing the preferable effect, the extract compound of the present invention may be administered in a daily dosage of 0.1 to 500 mg/g and preferably 1 to 200 mg/g, and the administration may be conducted once a day or divided into multiple dosages. Therefore, the above dosage is not intended to restrict the scope of the present invention in any way.

The composition of the present invention may be administered to mammals, such as rats, mice, livestocks, human beings, and the like, through various routes. All manners of administration may be expected, and for example, the administration may be conducted orally, rectally, or by intravenous, intramuscular, subcutaneous, endometrial, or intracerebroventricular injection.

Further, the present invention provides the use of the *Humulus japonicus* extract for preparing an agent for preventing or treating metabolic disorders or fatty liver.

Further, the present invention provides a method for preventing or treating metabolic disorders or fatty liver, comprising administering an effective amount of *Humulus japonicus* extract to a subject in need thereof.

The metabolic disorder is characterized by being selected from the group consisting of obesity, diabetes, hypertension, and hyperlipidemia.

The *Humulus japonicus* extract itself, or a pharmaceutically acceptable salt thereof, may be administered in an effective amount through various routes including oral, percutaneous, intravenous, and intramuscular routes. As used herein, the term "effective amount" refers to the amount showing the effect of treating and preventing metabolic disorders or fatty liver when the composition is administered to a subject. As used herein, the term "subject" refers to an animal, preferably, particularly mammals including human beings, and may be a cell, tissue and organ, or the like originated from an animal. The subject may be a patient in need of treatment.

The *Humulus japonicus* extract or the pharmaceutically acceptable salt thereof of the present invention may be administered per se, or may be administered through various dosage forms as described above, and preferably may be administered until a desired effect, that is, the effect of preventing or treating metabolic disorders or preventing or treating fatty liver is achieved. The extract compound and the pharmaceutically acceptable salt thereof of the present invention may be administered various routes by methods known in the art. That is, the extract compound and the pharmaceutically acceptable salt thereof of the present invention may be administered orally or parenterally, for example, intrabuccally, intramuscularly, intravenously, intradermally, intraarterially, intramedullarily, intrathecally, intraperitoneally, intranasally, intravaginally, intrarectally, sublingually, or subcutaneously, or may be administered through the gastrointestinal tract, mucous, or respiratory tract. For example, the *Humulus japonicus* extract or the pharmaceutically acceptable salt thereof of the present invention may be directly applied to the skin. Alternatively, the *Humulus japonicus* extract may be prepared in a preparation for injection, which is then injected in a predetermined amount under the skin using a 30-gauge injection needle, or the *Humulus japonicus* extract may be administered by lightly pricking with an injection needle on the skin, and preferably, may be directly applied to the skin. In addition, the *Humulus japonicus* extract and the pharmaceutically acceptable salt thereof of the present invention may be bound with molecules inducing high-affinity binding or may be administered in an encapsulated form into target cells or tissues (e.g., skin cells or skin tissues). The *Humulus japonicus* extract and the pharmaceutically acceptable salt thereof of the present invention may be bound with sterols (e.g., cholesterols), lipids (e.g., cationic lipids, virosomes, or liposomes), or target cell specific binders (e.g., ligands recognized by target cell specific receptors). Suitable coupling agents or cross-linking agents may include, for example, protein A, carbodiimide, N-succinimidyl-3-(2-pyridyldithio)propionate (SPDP), and the like.

These preparations are described in a literature well known in pharmaceutical chemistry (*Remington's* Pharmaceutical Science, 15th Edition, 1975, Mack Publishing Company, Easton, Pa.).

The present invention is directed to a composition containing a *Humulus japonicus* extract as an active ingredient for preventing or treating metabolic disorders, and more specifically, to a functional health food containing a *Humulus japonicus* extract as an active ingredient for preventing or improving metabolic disorders or for weight loss; to a pharmaceutical composition containing a *Humulus japonicus* extract as an active ingredient for preventing or treating metabolic disorders; to a functional health food or a pharmaceutical composition containing a *Humulus japonicus* extract as an active ingredient for preventing or improving fatty liver; and to a functional health food containing a *Humulus japonicus* extract as an active ingredient for inhibiting the accumulation of visceral fat. The *Humulus japonicus* extract of the present invention can reduce body weight, lower the level of blood lipid, ALT and AST. Further, the *Humulus japonicus* extract of the present invention has an effect of inhibiting the accumulation of visceral fat. The *Humulus japonicus* extract of the present invention is effective in preparing a functional health food for preventing or improving metabolic disorders, fatty liver, the accumulation of visceral fat, etc., by using these effects. However, the following examples are merely for illustrating the present invention and are not intended to limit the scope of the present invention.

EXAMPLE 1

Preparation of *Humulus japonicus* extract 1000 g of *Humulus japonicus* (Woori pharmaceutical Ltd., Seoul, Korea) was pulverized into a size of 30 meshes, and then put in 1000 ml of water, followed by heating at 100° C. for 2 hours. After the heating, the resultant solution was left for 1 hour to remove 10% (impurities, heavy metals etc.) of the lower phase and collect the upper phase, followed by freeze-drying, thereby obtaining 100 g of the *Humulus japonicus* extract.

EXAMPLE 2

Verification on the effect of *Humulus japonicus* extract in improving metabolic disorders <2-1> Preparation of Experimental Animals 40 male C57BL/6 mice (5-week old, Narabiotec) were purchased, and acclimatized with 12-hour light/dark cycle at 24±2° C. for 1 week. 40 mice were randomly divided into the following experimental groups of Table 1 each consisting of 10 mice. Test samples for the respective experimental groups were orally administered once daily. In addition, only the normal group was fed with a general feed for 12 weeks, but the other experimental groups were fed with a high-fat feed containing 60% fat (manufactured by Research diets, trade name: D12492) for 12 weeks.

TABLE 1

| Experimental groups | | |
|---|---|---|
| Experimental groups | Test Samples | Diet |
| Normal group | Water 1 ml for 12 weeks | General feed |
| Obesity control group | Water 1 ml for 12 weeks | 60% high-fat feed |
| Omacor-administered group | First four weeks: water 1 ml/5th-12th week: 2 g/kg/day, oral administeration of Omacor | 60% high-fat feed |
| *Humulus japonicus*-administered group | First four weeks: water 1 ml/5th-12th week: 1 g/kg/day, Oral administration of *Humulus japonicus* extract | |

Omacor supplied to the Omacor-administered group is a DHA-containing product developed by a Norwegian based Pronova Company, and is among a new series of secondary preventative drugs after post-hypertriglyceridemia and post-myocardial infarction, which is the most recently approved as prescription medicine from the FDA. The Omacor product has been verified to have high effectiveness of lowering the triglyceride level by 45% for those having hypertriglyceridemia and lowering the cardiovascular disease death rate by at least 30% when taken for the purpose of secondary prevention after post-myocardial infarction.

<2-2> Weight measurement and result analysis

Body weight was measured twice a week for each group. The average of body weight values measured twice a week for each group is shown in FIG. 1.

As can be seen in FIG. 1, the body weight of the obesity control group significantly increased when compared with the normal group. The *Humulus japonicus* administered group and the Omacor-administered group showed similar average values. Considering that the dosage of the Omacor-administered group was 2 times higher than that of the *Humulus japonicas*-administered group, the *Humulus japonicus* extract had more excellent efficacy than Omacor.

<2-3> Measurement of blood lipid level

After the administration for 12 weeks, the blood was collected from the posterior vena cava of the experimental animals, and the plasma was isolated from the collected blood through centrifugation, followed by measurements of high density lipoprotein cholesterol (HDL, Measurement method: Selective elimination (Wako Ind, Japan)), low density lipoprotein cholesterol (LDL, Measurement method:

Lactate to pyruvate (Backman Coulter, Ireland)), total cholesterol (TC, Measurement method: Enzymatic (Backman Coulter, Ireland)), and triglyceride (TG, Measurement method: Enzymatic (Wako Ind, Japan)).

The measurement results are shown in FIGS. 2 to 5.

<2-4> Histological observation of lipocytes

The subcutaneous fat was taken from the inguinal region of experimental animals, fixed in a 10% formalin solution, frozen, and then sliced into a 4 um thickness. The sliced tissues were stained with Hematoxylin & Eosin solution, followed by microscope observation. The results are shown in FIG. 9.

Figure 9:
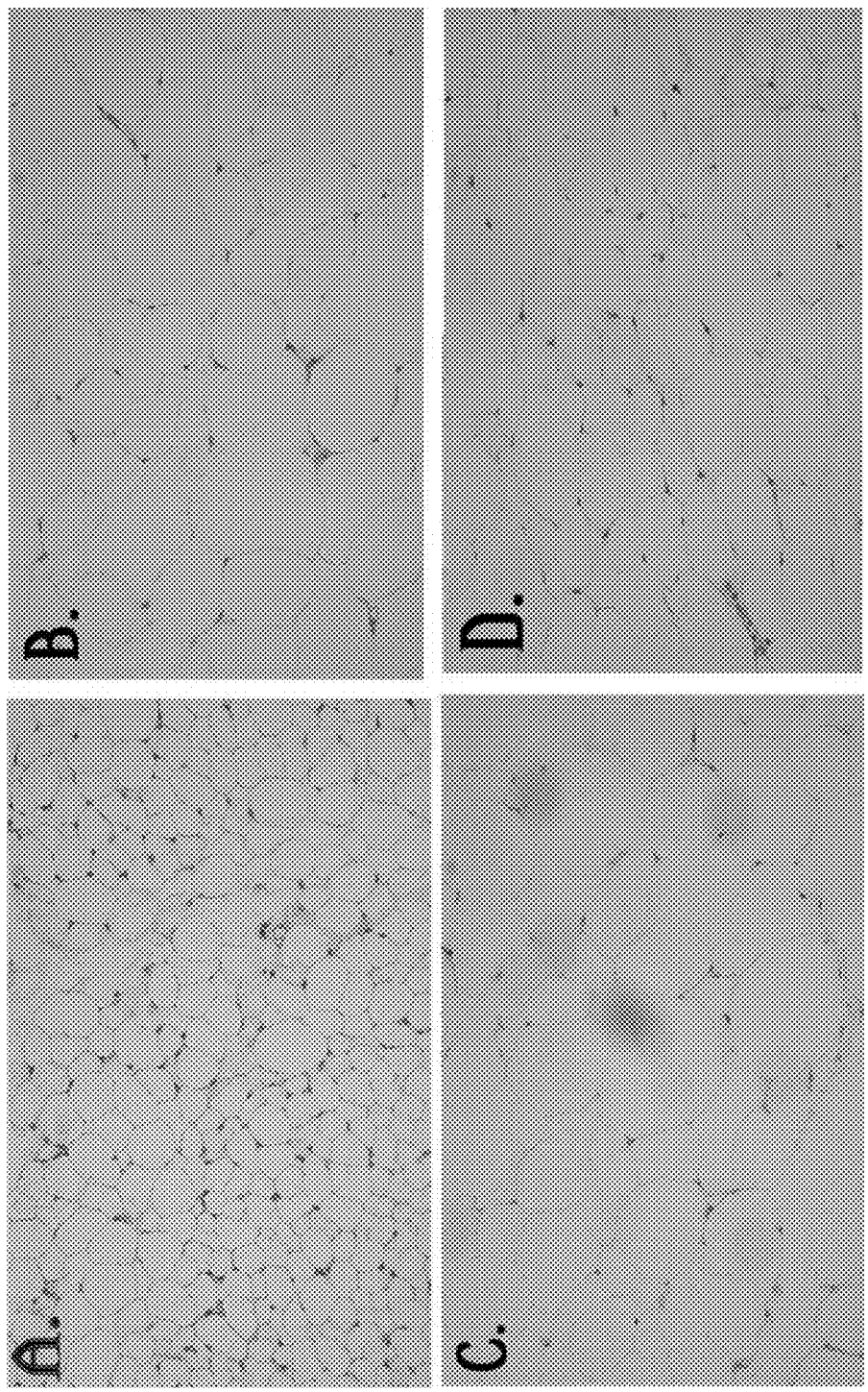
FIG. 9 is an image obtained by observing subcutaneous fat tissue slices from the inguinal regions of experimental animals. (A—normal group, B—obesity control group, C—Omacor-administered group, D—*Humulus japonicas*-administered group)
Figure 10:
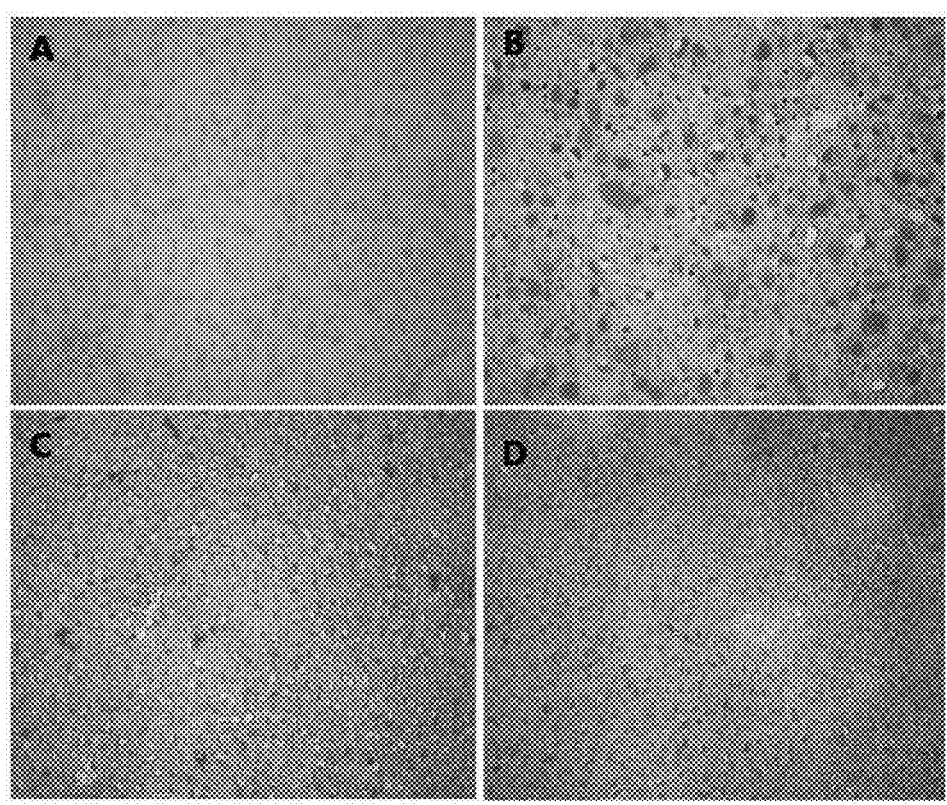
FIGS. 10A-10D are images obtained by observing liver tissue slices from experimental animals. Red parts indicate lipids. (A—normal group, B—obesity control group, C—Omacor-administered group, D—*Humulus japonicas*-administered group)

According to the analysis results from FIG. 9, only nuclei (dark-colored points) among cellular components are shown in the lipocytes. As for the normal group, the lipocytes are small, and nuclei can be seen in most lipocytes. However, as for the obesity control group, the lipocytes are very large, and a considerable number of lipocytes lack nuclei. It is assumed that lipocytes are enlarged in a restricted space and surrounding fatty tissues burst, resulting in loss of nuclei. The Omacor-administered group is not different from the obesity control group in light of lipocytes, but when compared with the obesity control group and the Omacor-administered group, the lipocytes are conspicuously small and the number of normal lipocytes is remarkably large in the *Humulus japonicas*-administered group.

EXAMPLE 3

Verification on the effect of *Humulus japonicus* extract in improving fatty liver <3-1> Measurement of liver weight After the experimental animals were fasted for 12 hours prior to their sacrifice, and then anesthetized with ether. The abdomen was cut open along the abdominal midline, and the blood was collected from the main abdominal artery to sacrifice the animals by blood loss. Then, the liver was perfused with physiological saline of 4° C. through the hepatic portal vein to remove the blood remaining in the tissues. Then, the liver was enucleated, and washed with physiological saline, and then the physiological saline remaining in the liver was removed, followed by weight measurement.

The weight average for each experimental group is shown in FIG. 6.

<3-2> Measurement of serum ALT and AST Activities

The blood collected while the abdomen was cut open was left at room temperature for 30 minutes to separate serum, and then alanine aminotransferase (ALT) and aspartate aminotransferase (AST) activities were measured. The activity measurement was conducted according to the methods of <Kang et al, Food Chem. Tox., 2011, 2453-2458>, and UV without P5P (Backman Coulter, Ireland) was used as a kit reagent.

Figure 7A:
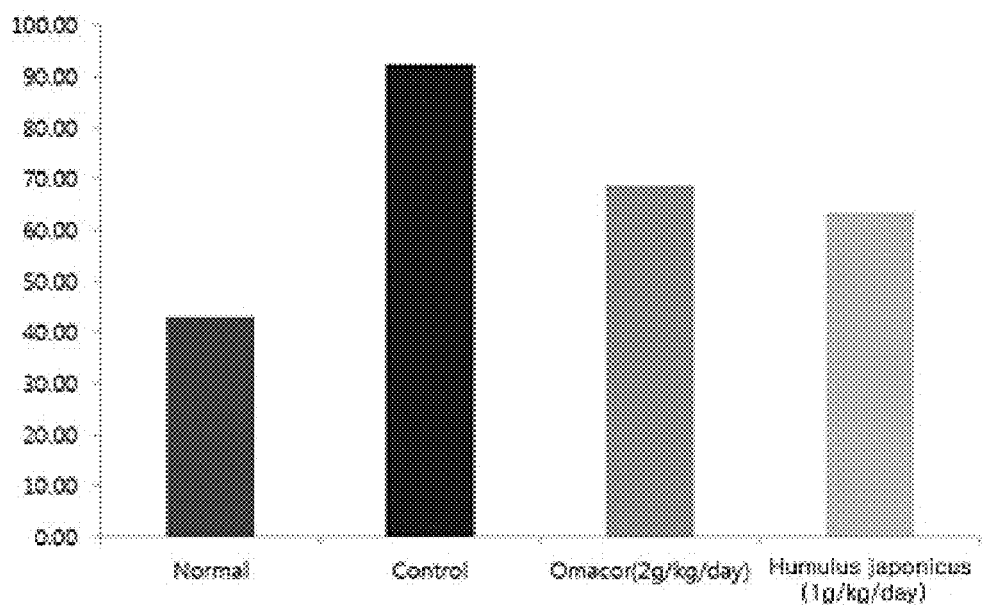
FIG. 7A is a graph depicting the comparison of serum ALT level among respective experimental groups. (Y-axis unit: IU/L/X axis: Normal (normal group), Control (obesity control group, Omacor (Omacor-administered group), *Humulus japonicus* (*Humulus japonicas*-administered group))
Figure 7B:
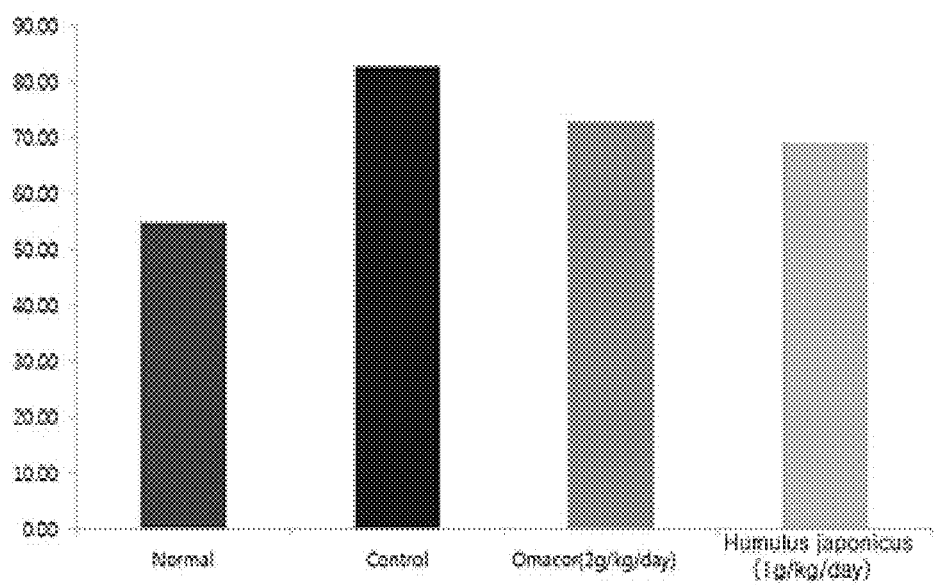
FIG. 7B is a graph depicting the comparison of serum AST level among respective experimental groups. (Y-axis unit: IU/L/X axis: Normal (normal group), Control (obesity control group, Omacor (Omacor-administered group), *Humulus japonicus* (*Humulus japonicas*-administered group))

The averages of ALT and AST levels for each experimental group are shown in FIGS. 7A and 7B.

<3-3> Histological observation of hepatocytes

The liver enucleated in Example 3-1 above was fixed in a 10% formalin solution, frozen, and then sliced into a 10 um thickness. The sliced tissues were stained with Hematoxylin & Eosin solution, and then only lipid was colored into red through Oil red O staining, followed by microscope observation. Images obtained by microscope observation are shown in FIGS. 10A-10D.

It can be confirmed from FIGS. 10A-10D that, as for the obesity control group, many lipid sites which were colored into red are observed among the hepatocytes, and a significantly large amount of fat was accumulated. The Omacor-administered group and the *Humulus japonicus*-administered group showed many reduced red areas, and particularly, the *Humulus japonicus* administered group showed a remarkably reduced red area.

EXAMPLE 4

Verification on the effect of *Humulus japonicus* extract in inhibiting visceral fat accumulation—measurement of mesenteric fat weight When the abdomen was cut open in Example 3, the mesenteric fat was also enucleated, and then washed with physiological saline, followed by weight measurement. The average of measurement values for each experimental group is shown in FIG. 8.

What is claimed is:

1. A method for treating obesity or hyperlipidemia in a male subject in need thereof, the method comprising administering an effective amount of a *Humulus japonicus* extract to said male subject,
    wherein the *Humulus japonicas* extract is a water extract or an ethanol extract.

2. The method of claim 1, wherein the male subject is a mammal.

3. The method of claim 2, wherein the mammal is selected from the group consisting of a rat, a mouse, livestock, and a human.

* * * * *